US011419863B2

(12) United States Patent
Leader

(10) Patent No.: US 11,419,863 B2
(45) Date of Patent: Aug. 23, 2022

(54) COMPOSITION CONTAINING APOMORPHINE AND A DIVALENT METAL CATION

(71) Applicant: Britannia Pharmaceuticals Ltd., Reading (GB)

(72) Inventor: Ian Philip Leader, Hampshire (GB)

(73) Assignee: BRITANNIA PHARMACEUTICALS LIMITED, Reading (GB)

( * ) Notice: Subject to any disclaimer, the term of this patent is extended or adjusted under 35 U.S.C. 154(b) by 0 days.

(21) Appl. No.: 15/421,722

(22) Filed: Feb. 1, 2017

(65) Prior Publication Data

US 2017/0136002 A1 May 18, 2017

Related U.S. Application Data

(63) Continuation of application No. PCT/EP2015/001577, filed on Jul. 31, 2015.

(30) Foreign Application Priority Data

Aug. 1, 2014 (EP) ..................................... 14002689

(51) Int. Cl.
| | |
|---|---|
| *A61K 9/00* | (2006.01) |
| *A61K 9/08* | (2006.01) |
| *A61K 33/06* | (2006.01) |
| *A61K 47/02* | (2006.01) |
| *A61K 47/18* | (2017.01) |
| *A61K 47/20* | (2006.01) |
| *A61K 31/473* | (2006.01) |

(52) U.S. Cl.
CPC .......... *A61K 31/473* (2013.01); *A61K 9/0019* (2013.01); *A61K 9/08* (2013.01); *A61K 33/06* (2013.01); *A61K 47/02* (2013.01); *A61K 47/20* (2013.01)

(58) Field of Classification Search
CPC ...... A61K 9/0019; A61K 47/02; A61K 47/20; A61K 31/473; A61K 9/08; A61K 47/183
See application file for complete search history.

(56) References Cited

U.S. PATENT DOCUMENTS

| | | | | |
|---|---|---|---|---|
| 6,514,482 B1 * | 2/2003 | Bartus | ................... | A61K 9/0075 128/203.15 |
| 2003/0225031 A1 * | 12/2003 | Quay | ................... | A61K 9/0043 514/55 |
| 2009/0143474 A1 * | 6/2009 | Royal | ................... | A61K 9/0019 514/629 |
| 2011/0111011 A1 * | 5/2011 | Giovinazzo | .......... | A61K 9/0056 424/443 |
| 2011/0111101 A1 | 5/2011 | Giovinazzo et al. | | |
| 2012/0220544 A1 * | 8/2012 | Schneider | ............ | A61K 9/0043 514/25 |
| 2014/0128422 A1 | 5/2014 | Dey et al. | | |

FOREIGN PATENT DOCUMENTS

| | | | |
|---|---|---|---|
| CN | 102480958 A | 5/2012 | |
| EP | 2 545 905 A1 | 1/2013 | |
| EP | 2545905 A1 * | 1/2013 | .......... A61K 9/0019 |
| WO | 2017/055337 A1 | 4/2017 | |

OTHER PUBLICATIONS

Syabro, STN Accession No. 1971:518952, 1969.*
FDA Approved Labeling Text for NDA 011264 dated Jul. 20, 2010.*
FDA Patient information, Seikagaku Corporation, Gel-One, 2011. (Year: 2011).*
International Search Report and Written Opinion in PCT/EP2015/001577 on which this application is based, dated Dec. 7, 2015.
Translation of Taiwanese Office Action dated Dec. 27, 2018 in counterpart Serial No. 10721230190; 4 pages.
Khaliulin et al., Cardioprotective and Antioxidant Effects of Apomorphine; Free Radical Research, Jul. 2003, vol. 37, No. 7, pp. 721-730.
Laar et al., The Role of EDTA in Provoking Allergic Reactions to Subcutaneous Infusion of Apomorphine in Patients with Parkinson Disease: A Histologic Study; Movement Disorders, vol. 13, No. 1, 1998, pp. 52-55.
Kristina Malinovskaja et al. "Ion-exchange and iontophoresis-Controlled Delivery of Apomorphine", European Journal of Pharmaceutics and Biophamiaceutics, 2013, vol. 83, pp. 477-484 (8 pages) publication date: Dec. 1, 2012.
M.B.H. Youdim et al., "Iron Chelating, Antioxidant and Cytoprotective Properties of Dopamine Receptor Agonist; Apomorphine", J Neural Transm, Suppl, 2000, vol. 58, pp. 83-96 (14 pages).
Kathleen M. Kantak et al., " Enhancement of Apomorphine and l-Amphetamine-lnduced Behaviors by Magnesium", Pharmacology Biochemistry and Behavior, 1990, vol. 36, No. 1, pp. 29-33 (5 pages).
Package Leaflet of "APO-go® Ampoules 10 mg/mL; Solution for Injection or Infusion", AMP PIL UK-IRL25.lndd, Britannia Pharmaceuticals Ltd., 2018, pp. 1-2 (2 pages).
Michael Ikechukwu Ugwoke et al., "Toxicological Investigations of the Effects Carboxymethylcellulose on Ciliary Beat Frequency of Human Nasal Epithelial Cells in Primary Suspension Culture and in Vivo on Rabbit Nasal Mucosa", International Journal of Pharmaceutics, 2000, vol. 205, pp. 43-51 (9 pages).
Jeban Ganesalingam et al., "Apomorphine-Induced Necrotic Ulcers", Movement Disorders, Dec. 2011, vol. 26, No. 12, p. 2182 (1 page).
Lars Wojtecki et al., "Multiple subcutaneous abscesses and necroses due to Apomorphine pump treatment", Parkinsonism and Related Disorders, vol. 18, Elsevier Ltd., Feb. 16, 2012 (1 page).

(Continued)

*Primary Examiner* — Jean P Cornet
(74) *Attorney, Agent, or Firm* — Sughrue Mion, PLLC

(57) ABSTRACT

A composition containing apomorphine and a divalent metal cation, such as, for example, $Zn^{2+}$, $Ca^{2+}$, or $Mg^{2+}$, is disclosed. The composition contains apomorphine and the divalent metal cation in a molar ratio of 2 or less. Optionally, the composition contains an antioxidant. The composition can be prepared as a medicament for treating Parkinson's disease.

20 Claims, No Drawings

(56) References Cited

OTHER PUBLICATIONS

A. Dadban et al., "Necroses cutanees localisees aux points d'injection d'apomorphine, Cutaneous necrosis at apomorphine injection points", Annales de dermatologie et de venereologie, vol. 137, 2010, pp. 730-735 (6 pages).

Electronic Medicines Compendium (EMC), Retrieved from URL [https://web.archive.org/web/20110103022709/https://www.medicines.org.uk/EMC/medicine/12942/SPC/A POgo+AMPOULES+10mg+ml+Solution+for+Injection+or+Infusion/], archived on WayBackMachine database, Jan. 3, 2011 (7 pages).

U.S. Dept. Health and Human Services, Agency for Toxic Substances and Disease Registry, "Toxicological Profile for Barium and Barium Compounds", Aug. 2007, pp. i-xx, 1-184, A-1-D-3 (231 pages).

Robin A. Bernhoft, "Mercury Toxicity and Treatment: A Review of the Literature", Journal of Environmental and Public Health, 2012, vol. 2012, pp. 1-10 (10 Pages).

\* cited by examiner

COMPOSITION CONTAINING APOMORPHINE AND A DIVALENT METAL CATION

CROSS-REFERENCE TO RELATED APPLICATIONS

This application is a continuation of International Application No. PCT/EP2015/001577, filed Jul. 31, 2015, which claims the priority of European application EP 14002689.9, filed Aug. 1, 2014, and the entire content of both applications is incorporated herein by reference.

FIELD OF THE DISCLOSURE

The present disclosure relates to a composition containing apomorphine and a divalent metal cation, a process for preparing this composition, a composition obtainable by this process, and the use of said compositions as a medicament, in particular for diagnosing, preventing and treating Parkinson's disease.

BACKGROUND OF THE DISCLOSURE

Apomorphine (systematical name: (6aR)-6-methyl-5,6, 6a,7-tetrahydro-4H-dibenzo[de,g]quinoline-10,11-diol) is used as an emetic, as an antidote and for the diagnosis and the treatment of the Parkinson's disease. In case of the treatment of Parkinson's disease, apomorphine is administered by infusions or by injections subcutaneously (s.c.). The commercially available product APO-go® used for the treatment of Parkinson's disease is provided with a pH of 3 to 4.

However, the administration of apomorphine to patients in need thereof can lead to the side effect of coagulative necrosis.

SUMMARY OF THE DISCLOSURE

A technical problem underlying the present disclosure can be seen in avoiding the above disadvantage, i.e. coagulative necrosis.

This has been achieved by the composition according to an aspect of the present disclosure, which comprises apomorphine and a divalent metal cation in a molar ratio of 2 or less.

A further advantage of the composition is that it shows a relatively high stability with respect to apomorphine.

DETAILED DESCRIPTION OF THE EXEMPLARY EMBODIMENTS

In a particular exemplary embodiment, the molar ratio of apomorphine and the divalent metal cation is from 2.0 to 0.2, more particularly from 1.25 to 0.5, and even more particularly from 1.25 to 0.83.

In another exemplary embodiment, the composition comprises apomorphine and the divalent metal cation in a stoichiometric amount ±10%.

The term "in a stoichiometric amount ±10%" means that the divalent metal cation or, if more than one type of divalent metal cation is present, the total amount of divalent metal cations in the composition is present in the stoichiometric (equimolar) amount or in an excess of not more than 10% or in a deficit of not more than 10% in relation to apomorphine. Particularly, the deviation from the stoichiometric amount is not more than 5%, more particularly not more than 1%, even more particularly not more than 0.5%. That is, the molar ratio of apomorphine to divalent metal cation is 1:1 with the deviation of ±10% or less as pointed out above.

As a divalent metal cation, any metal cation having two positive charges can be used, which are pharmaceutically acceptable or do not cause any harm in the human body.

Typically, the composition according to an exemplary embodiment of the present disclosure contains a chelate comprising apomorphine as a ligand and the divalent metal cation as a central atom in the above amount, wherein one or more, in particular two, separate coordinate bonds are formed between the apomorphine and the divalent cation.

Chelation describes a particular way that ions and molecules bind metal ions. According to the International Union of Pure and Applied Chemistry (IUPAC), chelation involves the formation or presence of two or more separate coordinate bonds between a polydentate (multiple bonded) ligand and a single central atom. Usually these ligands are organic compounds, and are called chelants, chelators, chelating agents, or sequestering agents.

The molecule apomorphine has two hydroxyl groups. For forming the above-mentioned coordinate bonds, it is typical that at least one in particular both of the hydroxyl groups of the apomorphine involved in the formation of the coordinate bond are present in the deprotonated form. This can be achieved by suitably adjusting the pH value of the composition according to the present disclosure. The pH can be adjusted before or after apomorphine and the divalent metal cation have been mixed.

It is to be noted that the term "chelate" as used herein refers preferably to the typical structure involving the formation of coordinate bonds between the ligand and the central atom.

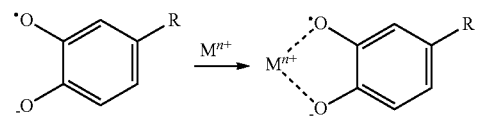

By this structure, the composition according to an exemplary embodiment of the present disclosure is distinguishable from solutions containing apomorphine and divalent metal cations, in which no chelate is formed, but the constituents apomorphine and divalent metal cation are present separated from each other.

Typically, at least 50% of the apomorphine contained in the composition of the disclosure are present in a chelated form with the divalent metal cation, more typically at least 80%, and even more typically at least 90%.

Also typically, water is present in the composition in particular as a solvent for the chelate compound formed by the apomorphine and the divalent metal cation. That is, the composition is an aqueous solution. This makes the composition according to the present disclosure suitable to be used as a medicament, for example for injection or as an infusion. For these applications, the composition shall be a sterile solution. Furthermore, it shall not contain any ingredients which are not pharmaceutically acceptable. Such a solution can be adapted to be used as an injection solution or as a concentrate for an infusion or directly itself as an infusion. Alternatively, such a solution can be adopted for buccal administration, the composition being a buccally absorbed liquid.

Preferably, the divalent metal cation is selected from one or more cations of the group consisting of $Ca^{2+}$, $Mg^{2+}$ and $Zn^{2+}$, which are particularly useful for avoiding coagulative necrosis as mentioned above.

In the composition according to the present disclosure, all three cations $Ca^{2+}$, $Mg^{2+}$ and $Zn^{2+}$ or the two cations $Ca^{2+}$ and $Mg^{2+}$ can be present. That is, the composition according to the present disclosure can contain apomorphine together with $Ca^{2+}$, $Mg^{2+}$ and $Zn^{2+}$ or together with $Ca^{2+}$ and $Mg^{2+}$.

Preferably, the composition according to the present disclosure contains apomorphine together with $Ca^{2+}$ and $Mg^{2+}$ wherein said two divalent metal cations are present in a ratio of 1.37:1 to 1.72:1, preferably 1.545:1. With this exemplary embodiment of the composition of the present disclosure, the occurrence of coagulative necrosis can be avoided very efficiently.

Preferably, the composition according to the present disclosure contains an antioxidant. The antioxidant is used to provide stability to the composition according to the present disclosure. That is, by using an antioxidant, in particular the exemplary antioxidants described in detail in the following, the composition according to the present disclosure has an auto-oxidation self-protecting effect.

The term "stability" as used hereinafter means generally that the composition according to the present disclosure containing the antioxidant is more stable than a composition not containing the antioxidant. The stability can be determined for example by visually inspecting a discoloration (darkening) over time being an indication of destabilization. The stability can be measured for example in that the composition is kept at room temperature or elevated temperature (e.g. 40° C.) over a certain period of time, e.g. 14 days and thereafter the discoloration (darkening) of the composition is determined e.g. by the naked eye.

In particular, the antioxidant has a sulfur group. Examples of such antioxidants are N-acetyl-L-cysteine and sodium-2-sulfanylethane sulfonate. With an antioxidant having a sulfur group in its molecule, the composition according to the present disclosure can be stabilized in a particular efficient way.

As antioxidant also other antioxidants than the above antioxidants having a sulfur group in its molecule can be used, for example ascorbic acid and sodium metabisulfite. With such antioxidants, the composition according to the present disclosure can also be stabilized efficiently.

The composition according to the present disclosure can contain at least one additive independently selected from the group consisting of cosolvent, surfactant, pH-adjuster, tonicifier and inert gas.

Examples of the cosolvent are polyethylene glycols (PEG), for example PEG 300, and propylene glycol. By adding cosolvents as additive to the composition according to the present disclosure, clear solutions can be obtained.

Examples of the surfactant are polysorbates, for example Polysorbat 80.

Examples of the tonicifier used for providing isotonisation are NaCl and/or carbohydrates, like glucose, mannitol or glycerol.

As an additive in the composition according to an exemplary embodiment of the present disclosure an inert gas can be present. An example of an inert gas is nitrogen. The inert gas can be used for removing oxygen from the composition according the present disclosure, which allows the amount of antioxidant to be lowered.

The amount of the additives can be easily determined by the skilled person by routine experiments with the aim to achieve the particular beneficial effect of the additive in view of its function.

As pointed out above, a pH adjuster can be present as an additive. Examples of the pH adjuster are HCl and NaOH which can be added to the composition according to the present disclosure depending on the pH to be adjusted. The pH range can be pH 3 to 10, with which a stability optimum can be achieved. Generally speaking, the pH of the composition according to the present disclosure is preferably adjusted to override the solubility barrier of pH 6.2 and being close to the physiological pH of 7.4.

According to another exemplary embodiment of the disclosure, the composition is a pharmaceutical solution or suspension, preferably a pharmaceutical solution for parenteral administration.

Typically, the composition has a concentration of apomorphine from 0.1 mg/ml to 50 mg/ml, more typically from 0.1 mg/ml to 40 mg/ml, even more typically from 0.1 mg/ml to 20 mg/ml, particularly from 1 mg/ml to 15 mg/ml, and more particularly from 3 mg/ml to 10 mg/ml.

The following Table 1 illustrates and exemplifies exemplary ingredients of the composition according to an exemplary embodiment of the present disclosure wherein it is to be explicitly noted that these ingredients are mentioned hereinafter independently from each other so that in the composition according to the present disclosure the following ingredients can be present independently from each other.

TABLE 1

| Ingredient | Function | Aim or Result | Requirement(s) |
| --- | --- | --- | --- |
| Apomorphine HCl (APO) | Active substance | Clear solution | No formation of particles |
| Water | Solvent | Clear solution | No formation of particles |
| Sodium metabisulfite (SM) | Antioxidant | Enhanced stability | |
| Ascorbic acid (AA) | Antioxidant | Enhanced stability | |
| N-Acetyl-L-cysteine (NAC) | Antioxidant | Enhanced stability | |
| Sodium-2-sulfanyl-ethane sulfonate (MESNA) | Antioxidant | Enhanced stability | |
| Polyethylene glycol 300 (PEG) and/or propylene glycol | Cosolvent | Clear solution | enhanced APO solubility and enhanced solubility of APO chelate with divalent metal cation |

TABLE 1-continued

| Ingredient | Function | Aim or Result | Requirement(s) |
|---|---|---|---|
| HCl | pH-adjuster | pH 3 - 6.2 | Adjust pH-stability optimum without formation of particles |
| NaOH | pH-adjuster | pH 3 - 6.2 | Adjust pH-stability optimum without formation of particles |
| NaCl | tonicifier (isotonisation) | Osmolality adjuster | |
| Carbohydrate (e.g. mannitol, glucose, glycerol) | tonicifier (isotonisation) | Osmolality adjuster | May also enhance APO solubility |
| $Zn^{2+}$ (preferably added as chloride) | Central atom in the chelate | lesser or no tanning (erythema, grade <4) | enhanced APO stability, formation of water soluble apomorphine complex without particles |
| $Ca^{2+}$ (preferably added as chloride) | Central atom in the chelate | lesser or no tanning (erythema, grade <4) | enhanced APO stability, formation of water soluble apomorphine complex without particles |
| $Mg^{2+}$ (preferably added as chloride) | Central atom in the chelate | lesser or no tanning (erythema, grade <4) | enhanced APO stability, formation of water soluble apomorphine complex without particles |
| Nitrogen | Oxygen removal | Lowering total oxygen and needed antioxidant amount | |

Typical compositions according to exemplary embodiments of the present disclosure are represented in the following Table 2:

TABLE 2

| APO | $H_2O$ | PEG | PS | SM | AA | NAC | MESNA | $Zn^{2+}$ | $Ca^{2+}$ | $Mg^{2+}$ | NaCl | Man | Gluc |
|---|---|---|---|---|---|---|---|---|---|---|---|---|---|
| X | X | X | | | | X | | | X | X | X | | |

"PS" means polysorbate
"Man" means mannitol
"Glu" means glucose
"X" means that the ingredient is present in the composition Remaining abbreviations are indicated in Table 1.

Typical compositions according to exemplary embodiments of the present disclosure can comprise the following ingredients in the following amounts:

1.) 5.00 mg/ml APO HCl (corresponding to 16.46 mmol/l APO)
    1.32 mg/ml $MgCl_2$ (corresponding to 6.50 mmol/l; as hexahydrate; Ph. Eur.)
    1.47 mg/ml $CaCl_2$ (corresponding to 10.0 mmol/l; as dihydrate, Ph. Eur.)

2.) 10.0 mg/ml APO HCl (corresponding to 32.92 mmol/l (APO)
    2.64 mg/ml $MgCl_2$ (corresponding to 13.0 mmol/l; as hexahydrate; Ph. Eur.)
    2.94 mg/ml $CaCl_2$ (corresponding to 20.0 mmol/l; as dihydrate, Ph. Eur.)

In contrast to hitherto known pharmaceutical preparations of apomorphine, the administration of the composition according to an exemplary embodiment of the present disclosure to a patient in need thereof does not cause coagulative necrosis. In other words, the severe drawback of the coagulative necrosis can be avoided by using the composition according to exemplary embodiments of the present disclosure in the diagnosis, prevention and treatment of diseases, e.g. the Parkinson's disease. The composition according to an exemplary embodiment of the present disclosure has generally speaking a good tissue protective effect. Furthermore, the composition according to an exemplary embodiment of the present disclosure has a very good bioavailability. Moreover, a very good tolerable apomorphine solution for injection/concentrate for continuous infusion in particular for the treatment of Parkinson is provided. Further, the storage stability is enhanced. The above mentioned advantages are achievable with the composition according to the present disclosure.

The present disclosure also relates to a process for preparing the composition as described above in detail, wherein the apomorphine and the divalent cation and optionally antioxidant and/or at least one of the additives are mixed together. The ingredients of the composition according to an exemplary embodiment of the present disclosure are described in detail above so that in so far it is referred to the above explanations.

The mixing is carried out in solution, preferably in a solution containing water as mentioned above. The order in which the ingredients are added to each other can be chosen by the skilled person according to the requirements of the particular case. For example, the apomorphine (in water) can be provided to which the divalent metal cations optionally contained in water can be added. Alternatively, the divalent metal cation (in water) can be provided and thereto the apomorphine, optionally in water, can be added.

The addition of the above-mentioned antioxidant and/or the above mentioned additive/s can be carried out during any stage of the above mixing of the apomorphine and the divalent metal cation.

Preferably, apomorphine is provided in an aqueous solution optionally with at least one of the above indicated additives and/or antioxidant. To this mixture, the divalent metal cation is added, followed by subsequently adjusting the pH, if necessary.

The above discussed composition according to an exemplary embodiment of the present disclosure cannot be further defined by indicating structural details as it has been done above. Therefore, it is suitable to define the product by the above process so that the subject matter of the present disclosure is also a composition containing the above mentioned ingredients and being obtainable by mixing them as explained above.

As pointed out above, apomorphine is used in the field of medicine, in particular Parkinson's disease. Therefore, the compositions according to an exemplary embodiment of the present disclosure can be used as a medicament, in particular for diagnosing, preventing and treating Parkinson's disease. The composition according to an exemplary embodiment of the present disclosure can therefore be provided in the form of a pharmaceutical preparation as commonly known by the skilled person, e.g in the form of a solution or a water soluble solid like buccal, tablet, waiver, ointment, transdermal plaster or powder for inhalation. In particular, the composition can be provided in a way to be used for injection, for example s.c. injection, or as a concentrate for continuous infusion as it is known in this field by the skilled person.

The present disclosure as outlined in detail above will be illustrated hereinafter by way of examples. It is explicitly pointed out that the following examples shall not be construed to restrict the present disclosure to the examples.

EXAMPLES

Examples 1 and 2 and Comparative Examples 1 and 2

The following compositions were prepared (the compound apomorphine is abbreviated as APO):

1.) 5.00 mg/ml APO HCl (corresponding to 16.46 mmol/l APO)
   1.32 mg/ml $MgCl_2$ (corresponding to 6.50 mmol/l; as hexahydrate; Ph. Eur.)
   1.47 mg/ml $CaCl_2$ (corresponding to 10.0 mmol/l; as dihydrate, Ph. Eur.)

2.) 10.0 mg/ml APO HCl (corresponding to 32.92 mmol/l APO)
   2.64 mg/ml $MgCl_2$ (corresponding to 13.0 mmol/l; as hexahydrate; Ph. Eur.)
   2.94 mg/ml $CaCl_2$ (corresponding to 20.0 mmol/l; as dihydrate, Ph. Eur.)

As a comparative example, commercially available APO-go® (5 mg/ml APO HCl) (=Comparative Example 1) and APO-go® (10 mg/ml APO HCl) (=Comparative Example 2) were used.

The compositions according to Examples 1 and 2 as well as according to Comparative Examples 1 and 2 were administered to various test persons. As a result, it was found that less coagulative necrosis was caused in the test persons receiving the compositions of Example 1 and 2 compared to the administration of compositions of Comparative Examples 1 and 2.

These results show that the compositions according to the present disclosure in which the apomorphine is present together with divalent metal cations suppress the adverse side effect of coagulative necrosis.

Stability Tests

To the above composition prepared according to Example 1 (C1) the antioxidant sodium metabisulfite (SM) in an amount of 2 mg/ml or the antioxidant N-acetyl-L-cysteine (NAC) in an amount of 4 mg/ml was added. The pH was adjusted to be in the range between 3 and 7. Discoloration (darkening, indication of destabilization) was observed with the naked eye after preparation of the composition (t=0), after 14 days stored at room temperature (14 d/RT) and after 14 days stored at 40° C. (14 d/40).

The results are summarized in the following Table 3.

TABLE 3

|  | pH = 3 | pH = 4 | pH = 5 | pH = 6 | pH = 7 |
| --- | --- | --- | --- | --- | --- |
| C1 (t = 0) | — | — | X | X | X |
| C1 (14d/RT) | X | X | X | X | X |
| C1 (14d/40) | X | X | X | X | X |
| C1 + SM (t = 0) | — | — | — | — | X |
| C1 + SM (14d/RT) | — | — | — | — | X |
| C1 + SM (14d/40) | — | — | — | — | X |
| C1 + NAC (t = 0) | — | — | — | — | X |
| C1 + NAC (14d/RT) | — | — | — | — | X |
| C1 + SM (14d/40) | — | — | — | — | X |

"—" means that no discoloration was observed with the naked eye
"X" means that discoloration was observed with the naked eye As can be seen from the above stability tests, the addition of an antioxidant does further improve the stability of the compositions according to the present disclosure.

The foregoing description of the exemplary embodiments of the disclosure illustrates and describes the present disclosure. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The invention claimed is:

1. A pharmaceutical composition comprising:
   (i) apomorphine as the sole active substance and
   (ii) divalent metal cations comprising $Ca^{2+}$ and $Mg^{2+}$ present in a ratio ranging from 1.37: 1 to 1.72: 1,
   the pharmaceutical composition having a molar ratio of apomorphine: the divalent metal cations ranging from 2 to 0.2,
   wherein the pharmaceutical composition is a pharmaceutical solution,
   wherein the pharmaceutical composition has a pH of 3-6.2.

2. The pharmaceutical composition according to claim 1, comprising apomorphine and the divalent metal cations in a stoichiometric amount ±10%.

3. The pharmaceutical composition according to claim 1, wherein the apomorphine as a ligand and one of the $Ca^{2+}$ and $Mg^{2+}$ as a central atom, form a chelate, wherein one or more separate coordinate bonds are formed between apomorphine and one of the $Ca^{2+}$ and $Mg^{2+}$.

4. The pharmaceutical composition according to claim 1, wherein water is present as a solvent for apomorphine and the divalent metal cations.

5. The pharmaceutical composition according to claim 1, the pharmaceutical composition having a concentration of apomorphine from 0.1 mg/ml to 40 mg/ml.

6. A medicament comprising the pharmaceutical composition as claimed in claim 1.

7. The pharmaceutical composition according to claim 1, wherein the molar ratio of apomorphine: the divalent metal cations range from 1.25 to 0.5.

8. The pharmaceutical composition according to claim 1, wherein the molar ratio of apomorphine: the divalent metal cations range from 1.25 to 0.83.

9. The pharmaceutical composition according to claim 1, wherein the pharmaceutical composition is a pharmaceutical solution for parenteral administration.

10. The pharmaceutical composition according to claim 5, having the concentration of apomorphine from 1 mg/ml to 15 mg/ml.

11. A pharmaceutical composition comprising:
(i) apomorphine as the sole active substance and
(ii) divalent metal cations comprising $Ca^{2+}$ and $Mg^{2+}$ present in a ratio ranging from 1.37: 1 to 1.72: 1,
the pharmaceutical composition having a molar ratio of apomorphine: the divalent metal cations ranging from 2 to 0.2,
wherein the pharmaceutical composition is a pharmaceutical solution.

12. The pharmaceutical composition according to claim 11, comprising apomorphine and the divalent metal cations in a stoichiometric amount ±10%.

13. The pharmaceutical composition according to claim 11, wherein the molar ratio of apomorphine: the divalent metal cation ranges from 1.25 to 0.5.

14. The pharmaceutical composition according to claim 1, wherein the pharmaceutical solution further comprises an antioxidant.

15. The pharmaceutical composition according to claim 1, wherein the pharmaceutical composition is a pharmaceutical solution that is an aqueous solution suitable for injection or infusion.

16. The pharmaceutical composition according to claim 1, wherein the ratio of $Ca^{2+}$ to $Mg^{2+}$ is 1.545 to 1.

17. The pharmaceutical composition according to claim 12, wherein the ratio of $Ca^{2+}$ to $Mg^{2+}$ is 1.545 to 1.

18. The pharmaceutical composition according to claim 1, wherein the divalent metal cations further comprise $Zn^{2+}$.

19. The pharmaceutical composition according to claim 11, wherein the divalent metal cations further comprise $Zn^{2+}$.

20. A method of treating Parkinson's disease comprising:
administering a pharmaceutical composition comprising:
(i) apomorphine as the sole active substance and
(ii) divalent metal cations comprising $Ca^{2+}$ and $Mg^{2+}$ present in a ratio ranging from 1.37: 1 to 1.72: 1,
the pharmaceutical composition having a molar ratio of apomorphine: the divalent metal cations ranging from 2 to 0.2,
wherein the pharmaceutical composition is a pharmaceutical solution, wherein the pharmaceutical composition has a pH of 3-6.2.

* * * * *